(12) United States Patent
Morita

(10) Patent No.: US 12,193,644 B2
(45) Date of Patent: Jan. 14, 2025

(54) ENDOSCOPE TREATMENT TOOL

(71) Applicant: OLYMPUS CORPORATION, Tokyo (JP)

(72) Inventor: Saki Morita, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 401 days.

(21) Appl. No.: 17/874,625

(22) Filed: Jul. 27, 2022

(65) Prior Publication Data

US 2022/0354344 A1  Nov. 10, 2022

Related U.S. Application Data

(63) Continuation of application No. PCT/JP2020/009450, filed on Mar. 5, 2020.

(51) Int. Cl.
*A61B 1/005* (2006.01)
*A61B 17/00* (2006.01)
*A61B 17/29* (2006.01)

(52) U.S. Cl.
CPC .... *A61B 1/0051* (2013.01); *A61B 2017/0034* (2013.01); *A61B 2017/2905* (2013.01);
(Continued)

(58) Field of Classification Search
CPC .............. A61B 1/00133; A61B 1/0051; A61B 2017/0034; A61B 2017/2905;
(Continued)

(56) References Cited

U.S. PATENT DOCUMENTS

2005/0250989 A1* 11/2005 Suzuki ............... A61B 1/00133
    600/106
2006/0149222 A1* 7/2006 Okada ................ A61B 17/2909
    606/1
(Continued)

FOREIGN PATENT DOCUMENTS

EP     3 222 241 A1    9/2017
JP   2008-253351 A   10/2008
(Continued)

OTHER PUBLICATIONS

International Search Report dated Jun. 2, 2020 received in PCT/JP2020/009450.

*Primary Examiner* — Jocelin C Tanner
(74) *Attorney, Agent, or Firm* — Scully, Scott, Murphy & Presser, P.C.

(57) ABSTRACT

An endoscope treatment tool that is insertable into a channel of an endoscope includes: an insertion unit having flexibility; and a treatment unit disposed on a distal end of the insertion unit and supported so as to be rotatable about a longitudinal axis of the insertion unit. The insertion unit includes a tubular exterior member configured to come into contact with the treatment unit on a distal end side of the insertion unit, the tubular exterior member configured to be moved in a direction of the longitudinal axis of the insertion unit, an operation member penetrating through an interior of the exterior member, the operation member configured to transmit rotation about the longitudinal axis to the treatment unit, and a wire penetrating through an interior of the insertion uni, the wire having a distal end fixed to the exterior member.

7 Claims, 16 Drawing Sheets

(52) U.S. Cl.
CPC .............. *A61B 2017/2929* (2013.01); *A61B 2017/2937* (2013.01)

(58) Field of Classification Search
CPC .... A61B 2017/2929; A61B 2017/2937; A61B 2017/2901; A61B 2017/2902; A61B 2017/2903; A61B 17/29; A61B 17/282; A61B 17/2908; A61B 17/2912; A61B 17/2927; A61B 17/2932
USPC ........................................................ 606/206
See application file for complete search history.

(56) References Cited

U.S. PATENT DOCUMENTS

| | | | |
|---|---|---|---|
| 2017/0105746 A1* | 4/2017 | O'Keefe | .......... A61B 17/00234 |
| 2017/0245842 A1 | 8/2017 | Ito et al. | |
| 2020/0069300 A1 | 3/2020 | Cruz et al. | |
| 2020/0170701 A1 | 6/2020 | Jonathan | |
| 2020/0305906 A1 | 10/2020 | Jonathan | |

FOREIGN PATENT DOCUMENTS

| | | | |
|---|---|---|---|
| JP | 2012-200415 A | 10/2012 | |
| WO | 2016/080180 A1 | 5/2016 | |
| WO | 2017/068074 A1 | 4/2017 | |

* cited by examiner

# ENDOSCOPE TREATMENT TOOL

CROSS-REFERENCE TO RELATED APPLICATIONS

This is a continuation of International Application PCT/JP2020/009450, with an international filing date of Mar. 5, 2020, which is hereby incorporated by reference herein in its entirety.

TECHNICAL FIELD

The present invention relates to an endoscope treatment tool.

BACKGROUND ART

An endoscope treatment tool that is inserted into a body cavity through an endoscope to treat tissues in the body cavity is known. (For example, see PTL 1.) This endoscope treatment tool comprises a tubular insertion unit to be inserted into a channel of an endoscope, an advanceable and retractable operation wire inserted into the insertion unit in the axial direction, and a treatment unit at a distal end of the operation wire.

An elastic member such as a spring is disposed at the distal end of the insertion unit. The elastic member urges the treatment unit toward the distal end side so as to lock relative rotation between the insertion unit and the treatment unit.

CITATION LIST

Patent Literature

{PTL 1} Japanese Unexamined Patent Application, Publication No. 2008-253351

SUMMARY OF INVENTION

An aspect of the present invention is directed to an endoscope treatment tool that is insertable into a channel of an endoscope, the endoscope treatment tool comprising: an insertion unit having flexibility; and a treatment unit disposed on a distal end of the insertion unit and supported so as to be rotatable about a longitudinal axis of the insertion unit, the insertion unit comprising: a tubular exterior member configured to come into contact with the treatment unit on an distal end side of the insertion unit, the tubular exterior member configured to be moved in a direction of the longitudinal axis of the insertion unit; an operation member penetrating through an interior of the exterior member, the operation member configured to transmit rotation about the longitudinal axis to the treatment unit; and a wire penetrating through an interior of the insertion unit, the wire having a distal end fixed to the exterior member.

According to this aspect, the treatment unit can be operated from outside the body, and the tissue in the body cavity can be treated through an endoscope by inserting the endoscope treatment tool into a channel of the endoscope inserted in the body cavity and by causing the treatment unit to project from the distal end of the endoscope. When the operator wishes to rotate the treatment unit about the longitudinal axis with respect to the insertion unit, the exterior member is moved in the axis direction of the insertion unit to separate the treatment unit from the exterior member. In this manner, the rotational force about the longitudinal axis applied to the operation member can be transmitted to the treatment unit, and the treatment unit can be rotated about the longitudinal axis with respect to the insertion unit.

Meanwhile, if it is desirable to restrict the rotation of the treatment unit about the longitudinal axis with respect to the insertion unit, the exterior member is moved in the axial direction of the insertion unit to bring the treatment unit into contact with the exterior member. In this manner, the frictional force generated by the contact restricts the rotation about the longitudinal axis with respect to the insertion unit, and unintended rotation of the treatment unit can be suppressed.

In other words, while the relative rotation between the moving unit and the treatment unit is unlocked without touching the operation wire, unintended rotation of the distal end side of the treatment unit that would occur upon unlocking of the relative rotation between the moving unit and the treatment unit can be suppressed.

Advantageous Effects of Invention

The present invention offers an advantage in that, while relative rotation between the insertion unit and the treatment unit is unlocked without touching the operation wire, unintended rotation of the distal end side that would occur upon unlocking of the relative rotation between the insertion unit and the treatment unit can be suppressed.

DESCRIPTION OF EMBODIMENTS

An endoscope treatment tool 1 according to one embodiment of the present invention will now be described with reference to the drawings.

Figure 1:
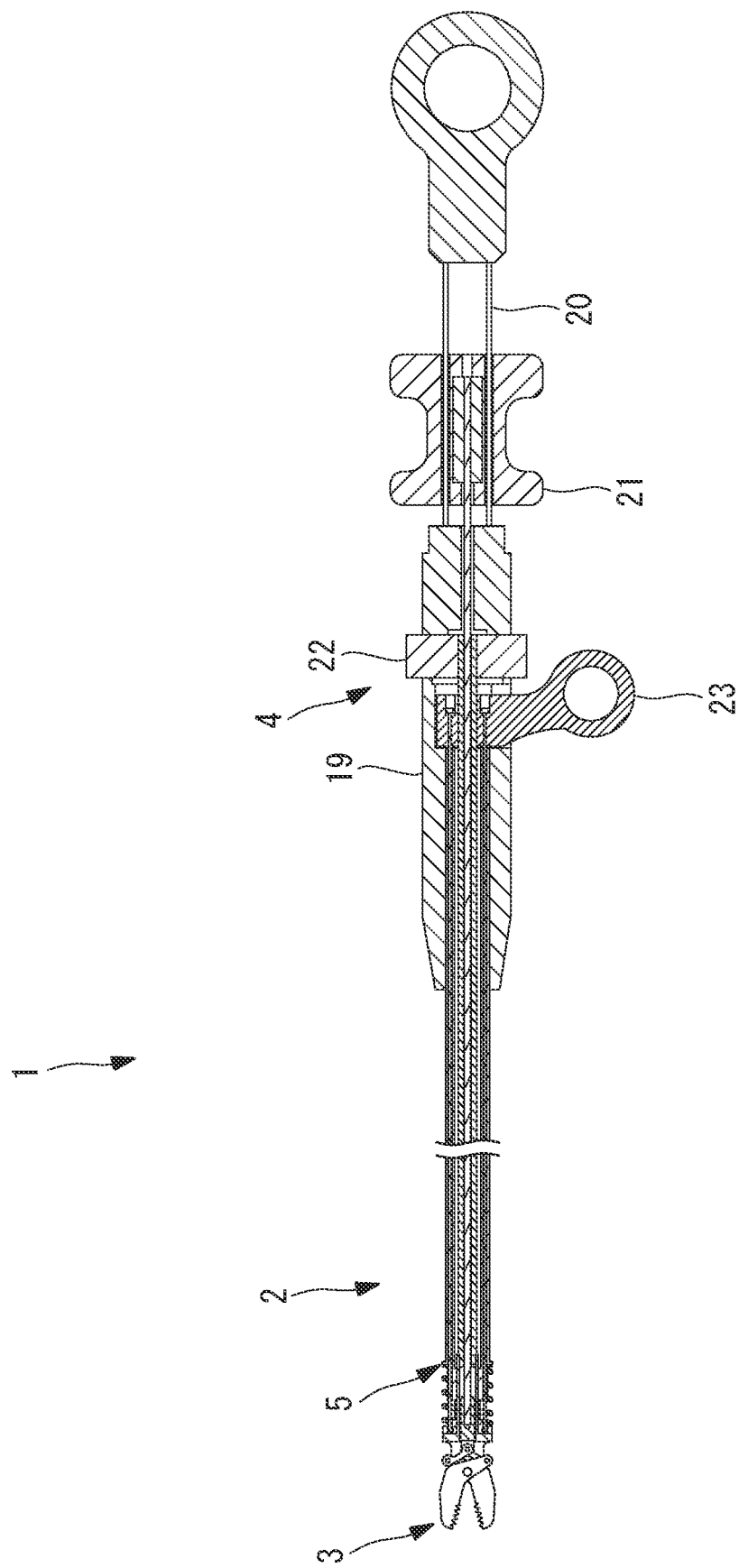
FIG. 1 is a longitudinal section of an endoscope treatment tool according to one embodiment of the present invention.

The endoscope treatment tool 1 of the present embodiment can be inserted into a channel of an endoscope, and, as illustrated in FIG. 1, comprises a long insertion unit 2, a treatment unit 3 supported on the distal end of the insertion unit 2 so as to be rotatable about the longitudinal axis, and an operation unit 4 disposed on the proximal end of an exterior member 5 of the insertion unit 2 described below.

Figure 2:
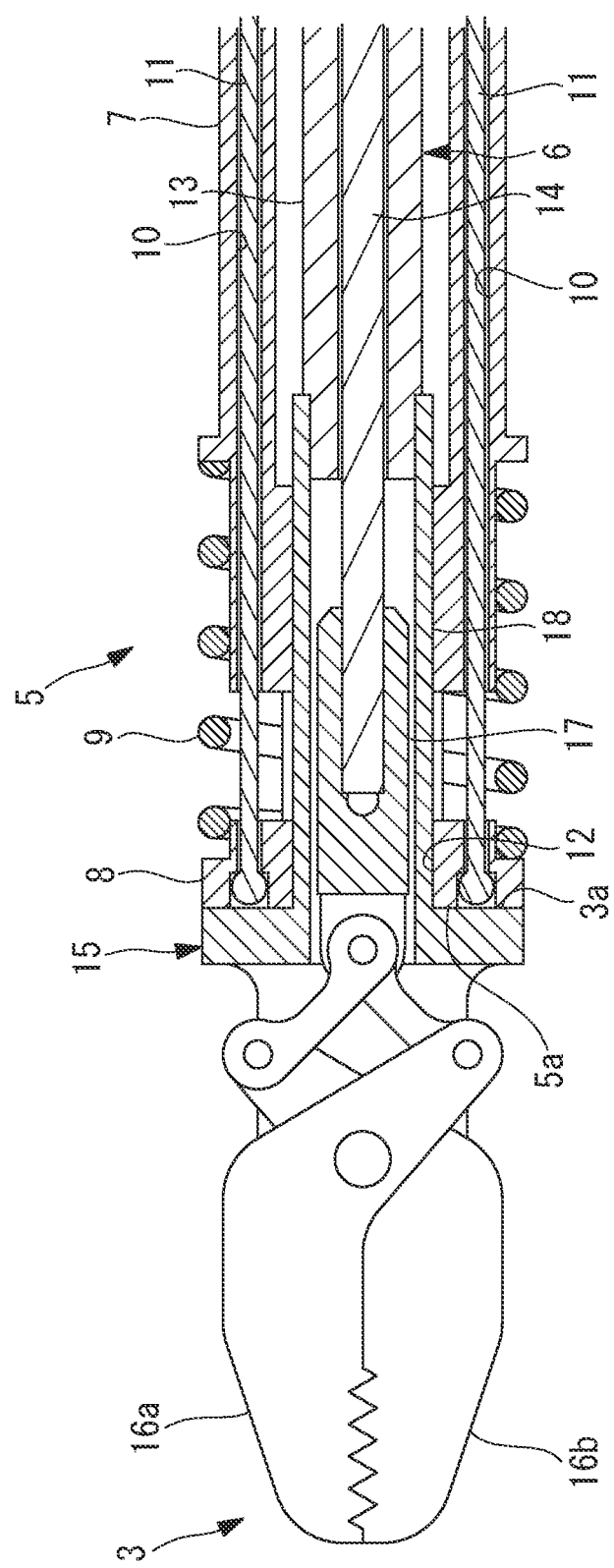
FIG. 2 is an enlarged longitudinal section of a distal end portion of the endoscope treatment tool illustrated in FIG. 1.

The insertion unit 2 is flexible. As illustrated in FIG. 2, the insertion unit 2 comprises a tubular exterior member 5, first wires (wires) 11 inserted into the insertion unit 2, and a long operation member 6 inserted into the exterior member 5.

The exterior member 5 comprises a tubular body 7 (for example, a sheath), a moving unit 8 which is a metal ring disposed at the distal end of the body 7, and a coil spring (urging member) 9 that is disposed between the body 7 and the moving unit 8 and that urges the moving unit 8 with respect to the body 7 in the forward longitudinal axis direction of the body 7.

The body 7 also has four lumens 10 at four positions equally spaced from each other in the circumferential direction, and these lumens 10 penetrate through the body 7 in the longitudinal axis direction. The first wires 11 are respectively inserted into the lumens 10 so as to be movable in the longitudinal direction. The distal ends of the first wires 11 each project forward from the distal end openings of the lumens 10 and are fixed to the moving unit 8. The moving unit 8 is formed into a ring plate shape having a center hole 12.

The operation unit 6 comprises a tubular torque tube (rotation transmitting member) 13, and a second wire (another wire) 14 inserted into the torque tube 13 so as to be movable in the longitudinal direction. The distal end of the torque tube 13 is fixed to the treatment unit 3. The distal end of the second wire 14 projects from the distal end opening of the torque tube 13, and is connected to the treatment unit 3.

The treatment unit 3 comprises a base 15, a pair of grasping pieces 16a and 16b supported on the base 15 so as to be pivotable about the axial line orthogonal to the longitudinal axis, and a link 17 that connects these grasping pieces 16a and 16b and the second wire 14. The base 15 includes a tubular part 18 that penetrates through the center hole 12 of the moving unit 8 and is fixed to the distal end of the torque tube 13, and a contact surface (proximal end surface) 3a that is on the distal end side with respect to the tubular part 18 and extends radially outward.

The tubular part 18 of the base 15 is allowed to pass through the center hole 12 so that the moving unit 8 is supported to be rotatable in the longitudinal axis direction by using the tubular part 18 as a guide. The contact surface 3a faces a distal end surface 5a of the moving unit 8. In this manner, due to the spring force of the coil spring 9, the distal end surface 5a of the moving unit 8 is pressed against the contact surface 3a.

As illustrated in FIG. 1, the operation unit 4 comprises a tubular operation unit body 19 to which the proximal end of the exterior member 5 is fixed, and a slider 21 that can be moved relative to the operation unit body 19 along a guide 20 that extends in the longitudinal axis direction on the proximal end side of the operation unit body 19. The operation unit 4 is further equipped with a disk-shaped dial 22 that is disposed at an intermediate position in the longitudinal axis direction of the operation unit body 19 and that is rotatably supported about the longitudinal axis with respect to the operation unit body 19, and a trigger 23 that is disposed on the distal end side of the dial 22 and that is rotatably supported about the longitudinal axis direction with respect to the operation unit body 19.

The proximal end of the second wire 14 is fixed to the slider 21.

The proximal end of the torque tube 13 is fixed to the dial 22.

The proximal ends of the four first wires 11 are fixed to the trigger 23.

Figure 3:
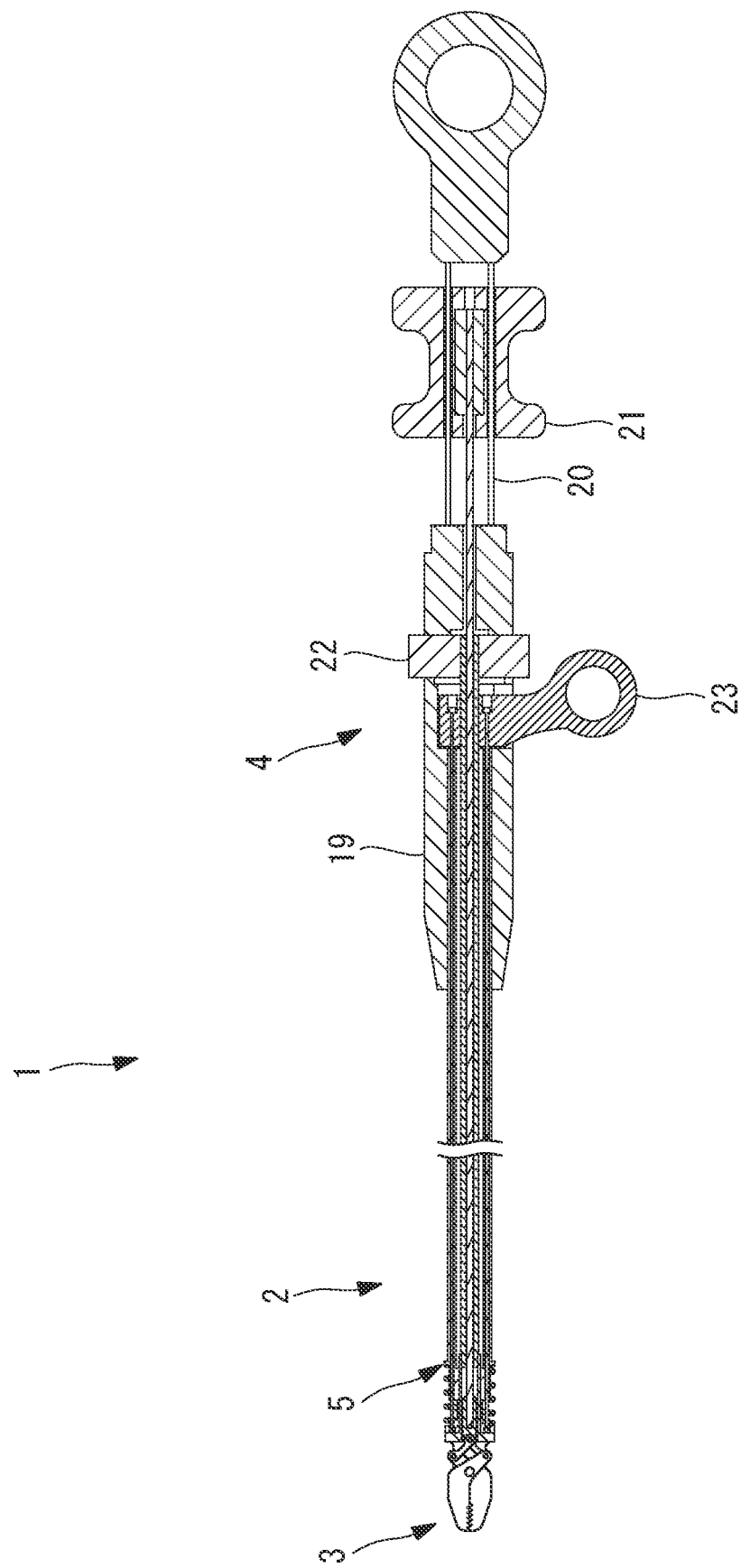
FIG. 3 is a longitudinal section of a treatment unit of the endoscope treatment tool in a closed state.

As illustrated in FIG. 3, in the operation unit 4 disposed at the proximal end of the insertion unit 2, a tension can be generated in the second wire 14 by moving the slider 21 toward the proximal end side with respect to the operation unit body 19, and thus the pair of grasping pieces 16a and 16b at the distal end of the insertion unit 2 can be closed.

Figure 4:
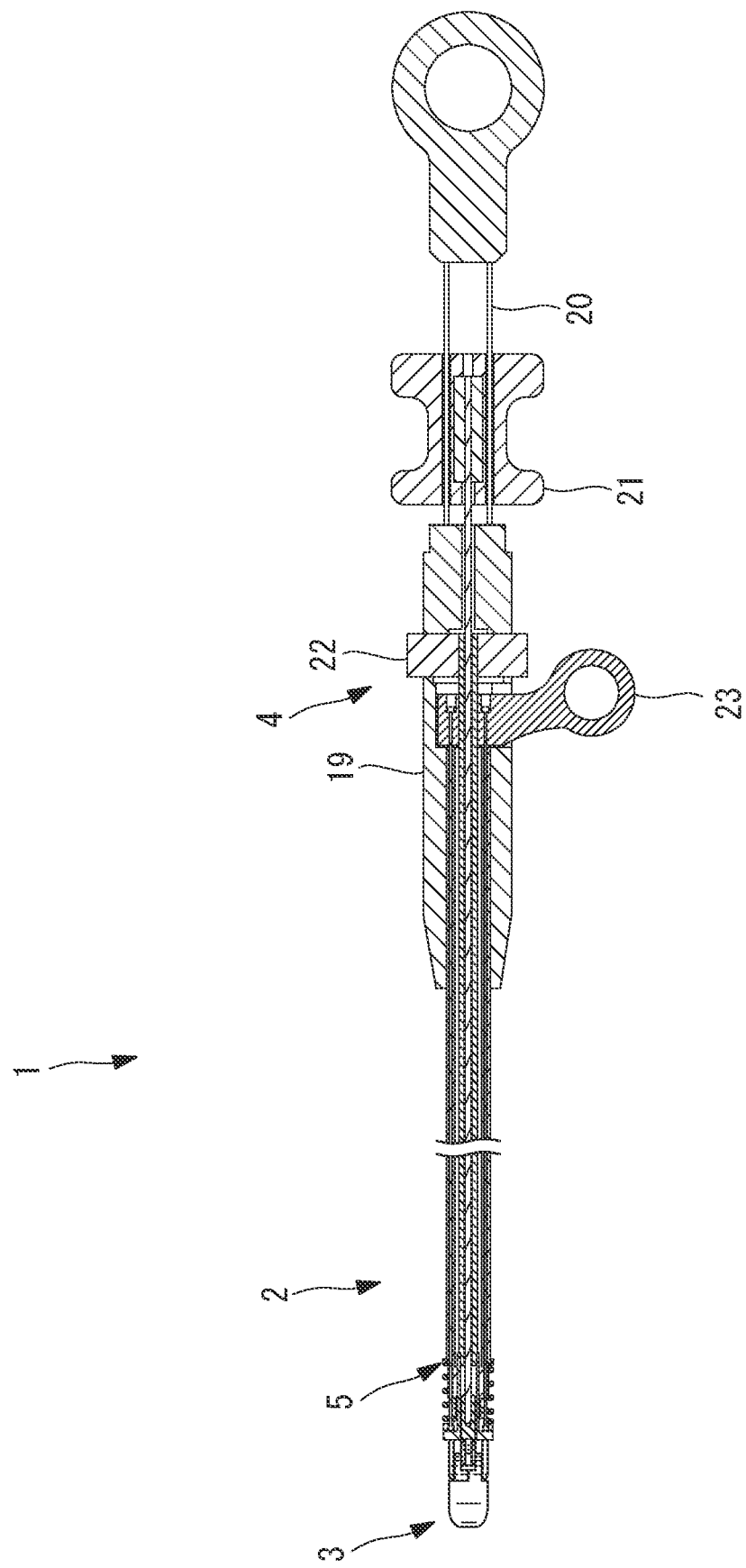
FIG. 4 is a longitudinal section illustrating the state in which the treatment unit of the endoscope treatment tool illustrated in FIG. 1 is rotated about a longitudinal axis.

As illustrated in FIG. 4, in the operation unit 4, a rotational force about the longitudinal axis can be applied to the torque tube 13 by rotating the dial 22 about the longitudinal axis with respect to the operation unit body 19, and thus the treatment unit 3 at the distal end of the insertion unit 2 can be rotated about the longitudinal axis.

Figure 5:
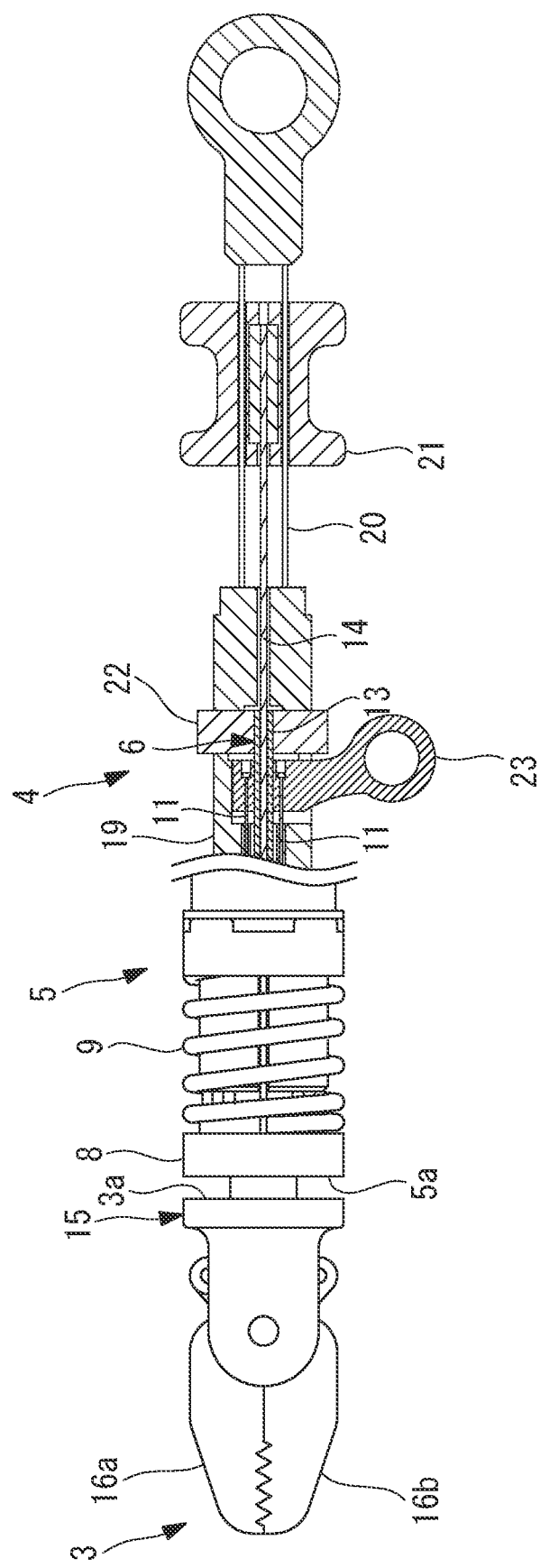
FIG. 5 is a diagram illustrating the state in which a moving unit and a base of the endoscope treatment tool illustrated in FIG. 1 are separated from each other.

As illustrated in FIG. 5, in the operation unit 4, a tension can be generated in the first wires 11 by moving the trigger 23 toward the proximal end side with respect to the operation unit body 19, and thus the moving unit 8 can be moved toward the proximal end side by resisting the spring force of the coil spring 9. The distal end surface 5a of the moving unit 8 can be moved away from the contact surface 3a of the base 15 of the treatment unit 3 by moving the moving unit 8 toward the proximal end side.

Figure 6:
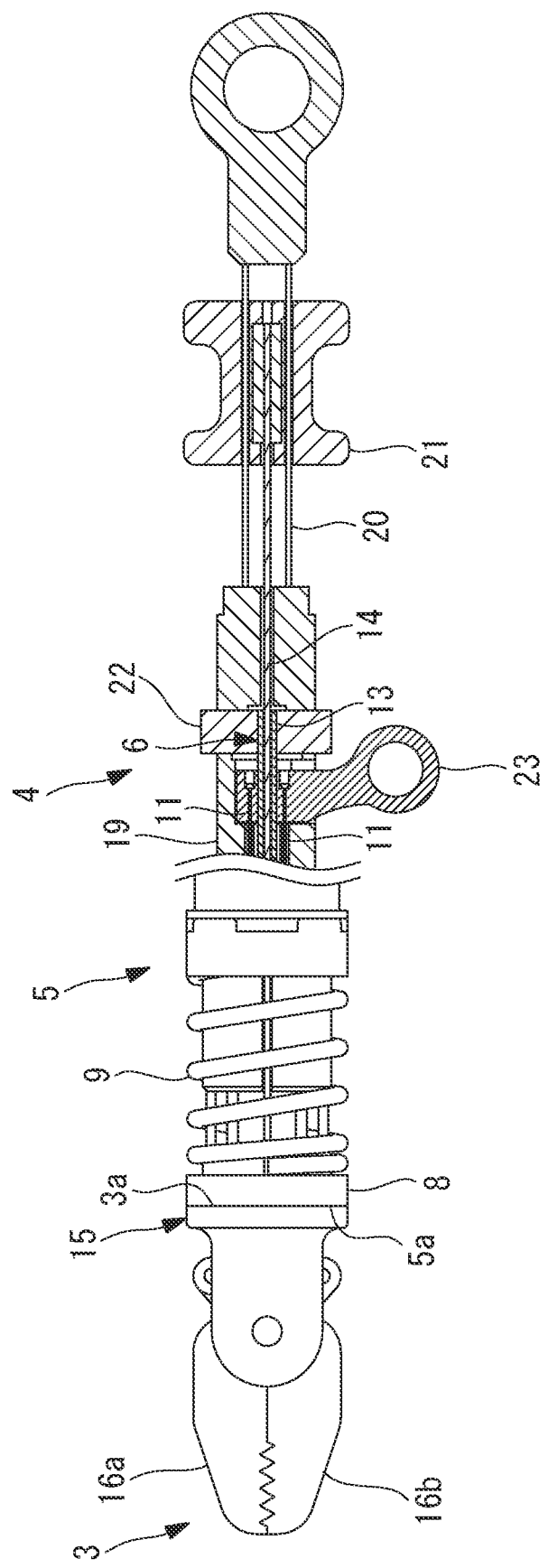
FIG. 6 is a diagram illustrating the state in which the moving unit and the base of the endoscope treatment tool illustrated in FIG. 1 are joined.

Meanwhile, as illustrated in FIG. 6, the moving unit 8 can be moved toward the distal end side due to the elastic restoring force of the coil spring 9 by releasing the force applied to the trigger 23, and thus the state in which the distal end surface 5a of the moving unit 8 is in close contact with the contact surface 3a of the base 15 can be maintained.

The operation of the endoscope treatment tool 1 of the present embodiment configured as such will now be described.

In order to perform treatment inside the body cavity of a patient by using the endoscope treatment tool 1 of the present embodiment, the endoscope treatment tool 1 is inserted into a channel of an endoscope inserted in the body cavity, and the treatment unit 3 is caused to project from the distal end opening of the channel. The treatment unit 3 is moved within the image acquired by the endoscope so as to approach the target site.

Referring now to FIG. 5, if the operator wishes to change the orientation of the treatment unit 3 about the longitudinal axis of the insertion unit 2 in this state, the operator pulls the trigger 23 toward the proximal end side with respect to the operation unit body 19. As a result, a tension is applied to the four first wires 11 connected to the trigger 23, and the moving unit 8 to which the distal ends of the first wires 11 are fixed moves toward the proximal end side. As a result, the distal end surface 5a of the moving unit 8 moves away from the contact surface 3a of the base 15 of the treatment unit 3.

In this state, the dial 22 is rotated with respect to the operation unit 19. As a result, a twisting force acts on the torque tube 13 fixed to the dial 22, and the twisting force transmitted through the torque tube 13 moves the treatment unit 3, which is fixed to the distal end of the torque tube 13, about the longitudinal axis of the insertion unit 2.

Thus, the orientation of the treatment unit 3 can be adjusted as desired by adjusting the position of the dial 22. Upon ending the adjustment of the orientation, as illustrated in FIG. 6, the grip on the trigger 23 is released to release the traction force that has been applied to the trigger 23. In this manner, due to the elastic restoring force of the coil spring 9, the distal end surface 5a of the moving unit 8 is pressed against the contact surface 3a of the base 15 of the treatment unit 3, and the frictional force between these surfaces maintains the angle (rotation amount) of the treatment unit 3 about the longitudinal axis with respect to the distal end surface 5a of the exterior member 5.

In this state, as illustrated in FIG. 1, the slider 21 is moved toward the distal end side with respect to the operation unit body 19 so as to open the pair of grasping pieces 16a and 16b and place the tissue between the grasping pieces 16a and 16b. In this state, as illustrated in FIG. 3, the slider 21 is moved toward the proximal end side with respect to the operation unit body 19 so that the pair of grasping pieces 16a and 16b close and grasp the tissue therebetween.

As described above, according to the endoscope treatment tool 1 of the present embodiment, the moving unit 8 and the base 15 can be disconnected from each other by applying a tension to the first wires 11. Meanwhile, the moving unit 8 and the base 15 connect to each other by the elastic restoring force of the coil spring 9 as the tension applied to the first wires 11 is released. Thus, there are advantages in that, compared to the case where the rotation of the distal end of the treatment unit 3 is unlocked by applying a tension to the torque tube 13 serving as the rotation transmitting member, a tension can be applied to the first wires 11 more reliably so as to unlock the relative rotation between the moving unit 8 and the base 15 without touching the rotation transmitting member 13, and unintended rotation of the distal end side upon unlocking of the relative rotation between the moving unit 8 and the base 15 can be suppressed.

Furthermore, by merely releasing the force applied to the trigger 23, the elastic restoring force of the coil spring 9 maintains the state in which the rotation of the treatment unit 3 about the longitudinal axis with respect to the insertion unit 2 is restricted. In this state, even when the torque urging the treatment unit 3 to rotate about the longitudinal axis acts on the treatment unit 3 from outside, unintended rotation of the treatment unit 3 with respect to the insertion unit 2 can be effectively prevented.

In other words, in a state where the moving unit 8 is separated from the contact surface 3a of the base 15, only the torque tube 13 supports the treatment unit 3. Typically, the torque tube 13 has a twisted wire structure or a coil structure and thus exhibits low torsional rigidity in the absence of a particular torsion; thus, the treatment unit 3 rotates easily if the torque from outside acts on the treatment unit 3. According to the present embodiment, the moving unit 8 is pressed against the contact surface 3a to allow the exterior member 5, which has higher rigidity than the torque tube 13, to support the treatment unit 3; thus, the rotation can be more reliably restricted.

In the present embodiment, the exterior member 5 comprises the body 7 and the moving unit 8, and allowing and restricting the rotation of the treatment unit 3 about the longitudinal axis are switched by moving the moving unit 8 in the longitudinal axis direction with respect to the body 7. Alternatively, as illustrated in FIGS. 7 and 8, the entire exterior member 5 may be moved.

In such a case, the exterior member 5 comprises the body 7, and the distal ends of the first wires 11 are fixed to the distal end portion of the body 7.

Figure 7:
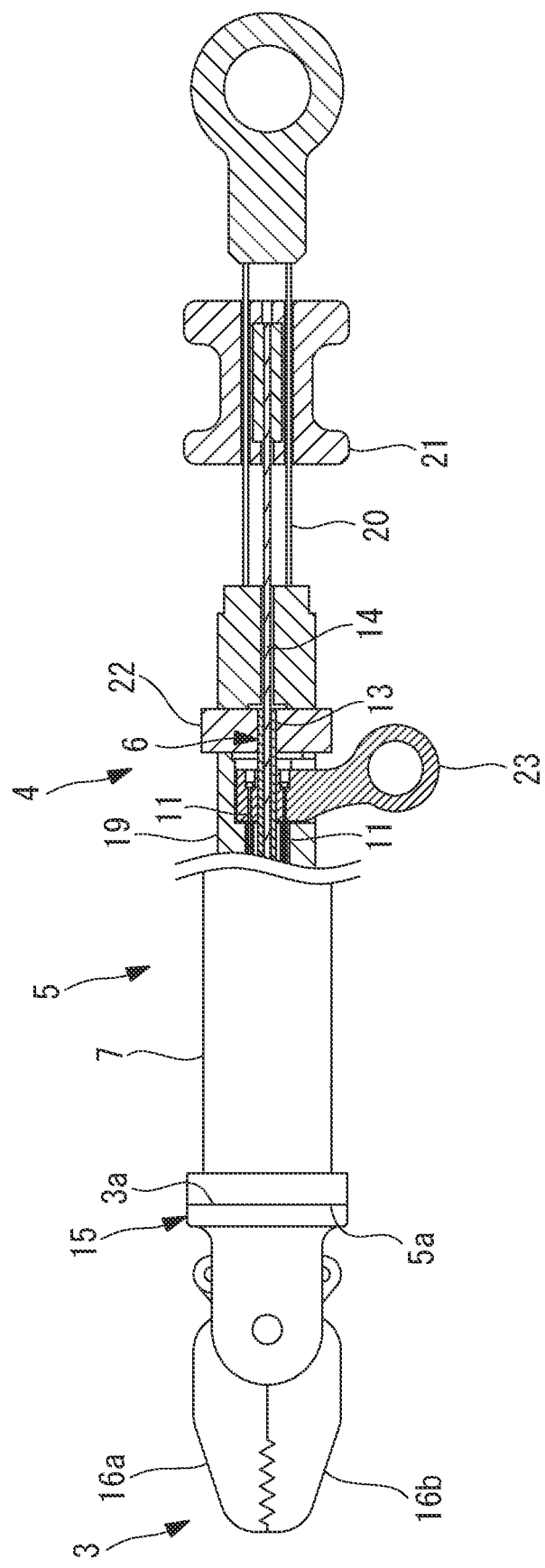
FIG. 7 is a diagram illustrating the state in which the moving unit and the base are joined in a first modification of the endoscope treatment tool illustrated in FIG. 1.

As illustrated in FIG. 7, in the operation unit 4, a tension is generated in the first wires 11 by moving the trigger 23 toward the distal end side with respect to the operation unit body 19, and the entire exterior member 5 can be moved toward the distal end side in the longitudinal axis direction with respect to the treatment unit 3 so as to press the distal end surface 5a of the exterior member 5 against the contact surface 3a of the treatment unit 3. In this manner, the flat distal end surface 5a comes into close contact with the flat contact surface 3a, and the frictional force between these surfaces maintains the angle (rotation amount) of the treatment unit 3 about the longitudinal axis with respect to the distal end surface 5a of the exterior member 5.

Figure 8:
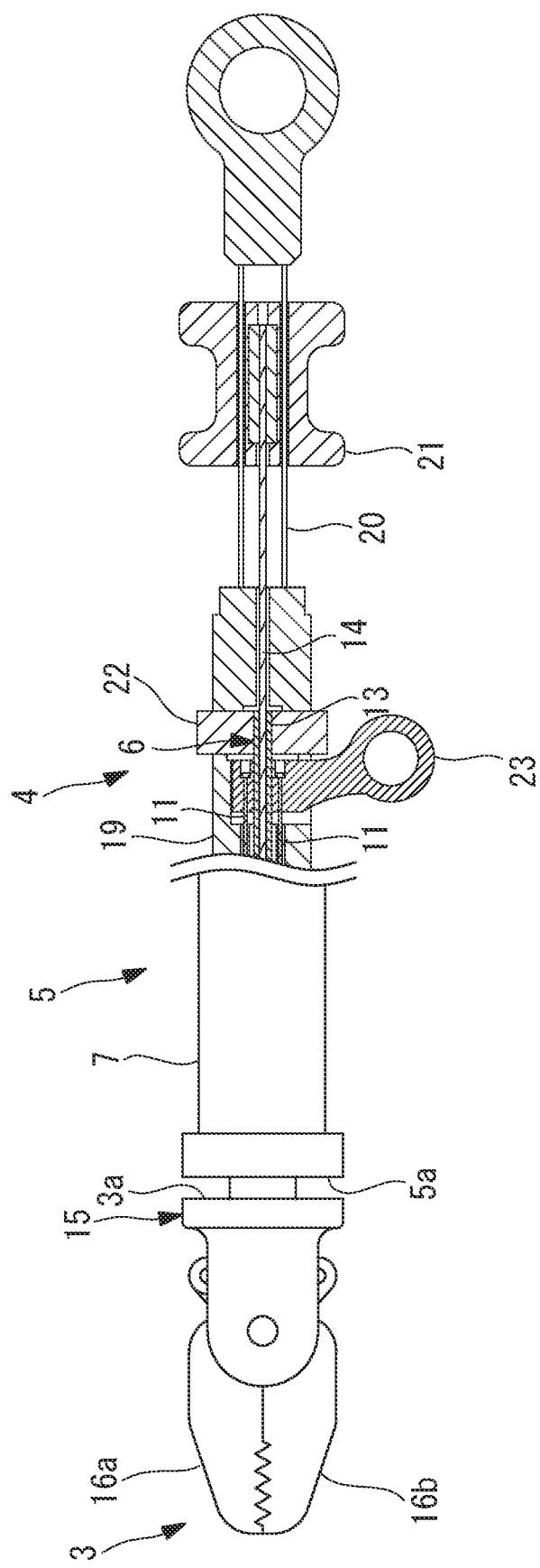
FIG. 8 is a diagram illustrating the state in which the moving unit and the base are separated from each other in the first modification of the endoscope treatment tool.

Then, as illustrated in FIG. 8, in the operation unit 4, a tension is generated in the first wires 11 by moving the trigger 23 toward the proximal end side with respect to the operation unit body 19, and thus the entire exterior member 5 can be moved toward the proximal end side in the longitudinal axis direction with respect to the treatment unit 3, and the distal end surface 5a of the exterior member 5 can be separated from the contact surface 3a of the treatment unit 3.

Figure 9:
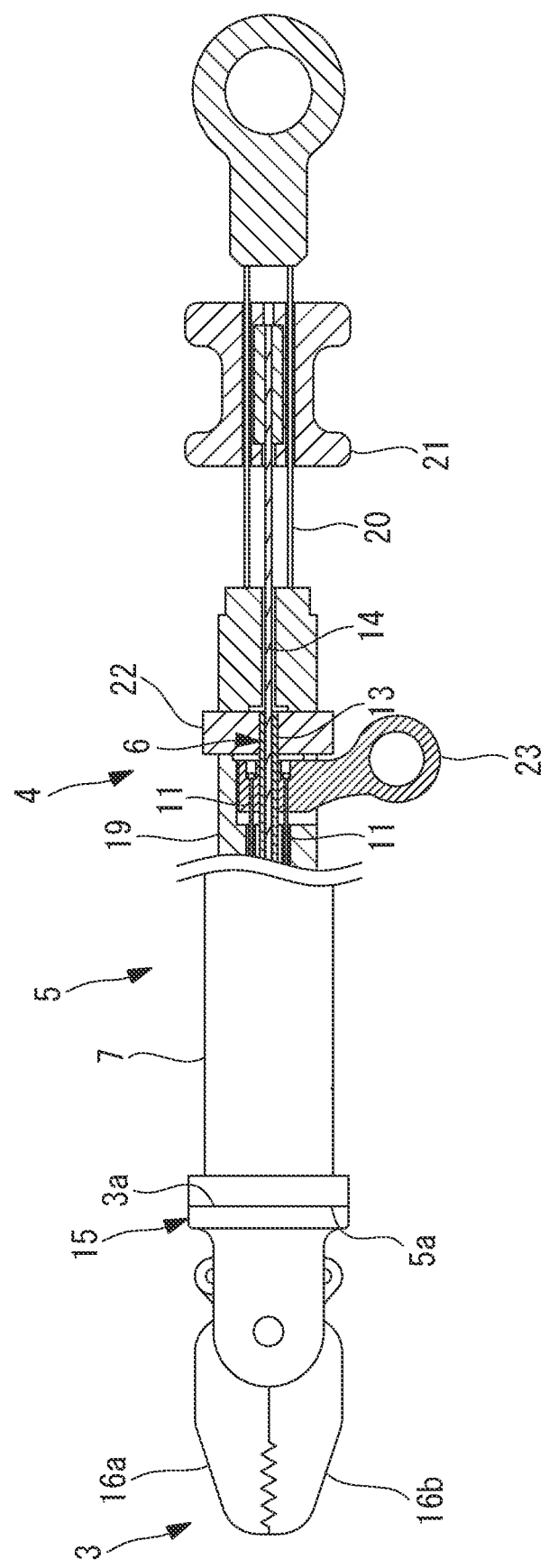
FIG. 9 is a diagram illustrating the state in which the moving unit and the base are joined in a second modification of the endoscope treatment tool illustrated in FIG. 1.
Figure 10:
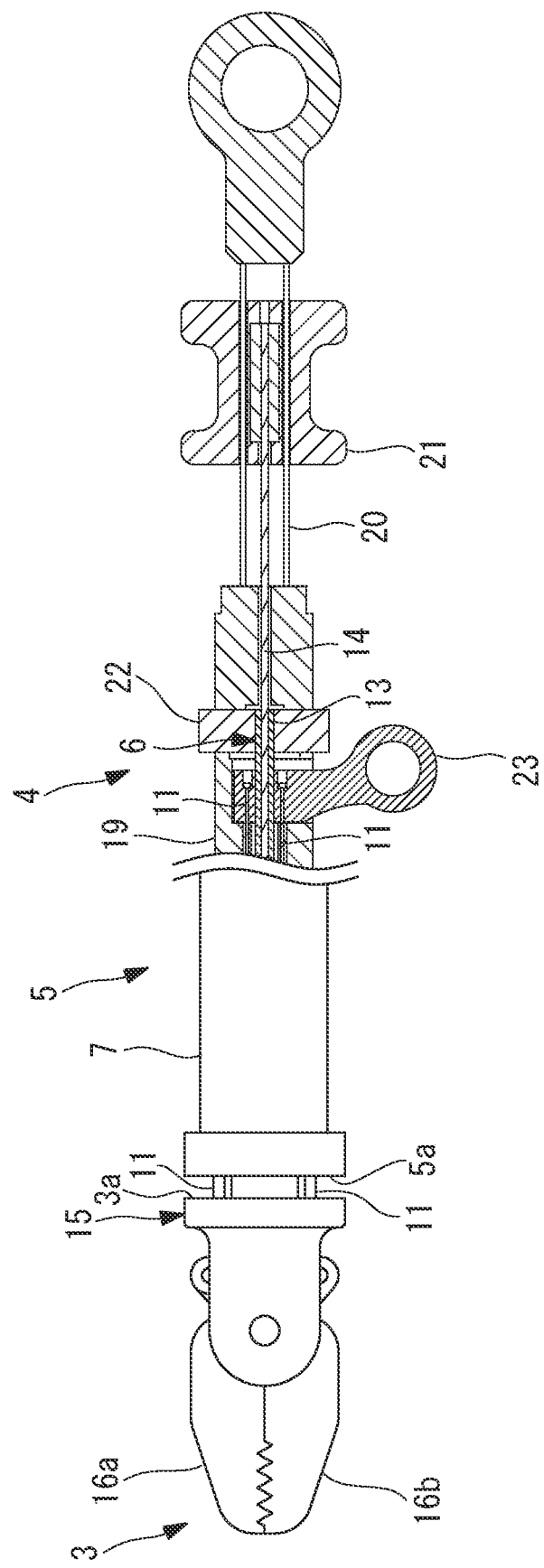
FIG. 10 is a diagram illustrating the state in which the moving unit and the base are separated from each other in the second modification of the endoscope treatment tool illustrated in FIG. 1.

Alternatively, as illustrated in FIGS. 9 and 10, the exterior member 5 may be fixed and the treatment unit 3 may be moved in the longitudinal axis direction instead of moving the moving unit 8 in the longitudinal axis direction with respect to the body 7.

In such a case, the exterior member 5 comprises the body 7, and the distal ends of the first wires 11 are fixed to the base 15 of the treatment unit 3.

As illustrated in FIG. 9, in the operation unit 4, a tension is generated in the first wires 11 by moving the trigger 23 toward the proximal end side with respect to the operation unit body 19, and thus the treatment unit 3 can be moved toward the proximal end side in the longitudinal axis direction with respect to the exterior member 5, and the contact surface 3a of the treatment unit 3 is pressed against the distal end surface 5a of the exterior member 5. In this manner, the flat distal end surface 5a comes into close contact with the flat contact surface 3a, and the frictional force between these surfaces maintains the angle (rotation amount) of the treatment unit 3 about the longitudinal axis with respect to the distal end surface 5a of the exterior member 5.

Then, as illustrated in FIG. 10, in the operation unit 4, a tension is generated in the first wires 11 by moving the trigger 23 toward the distal end side with respect to the operation unit body 19, and thus the treatment unit 3 can be moved toward the distal end side in the longitudinal axis direction with respect to the exterior member 5, and the contact surface 3a of the treatment unit 3 can be separated from the distal end surface 5a of the exterior member 5.

Furthermore, in the present embodiment, the rotation of the treatment unit 3 is restricted by the friction between the flat distal end surface 5a of the moving unit 8 and the flat contact surface 3a in close contact with each other; alternatively, the distal end surface 5a and the contact surface 3a need not be in close contact with each other as long as the distal end surface 5a and the contact surface 3a touch each other and a frictional force is generated.

Figure 11:
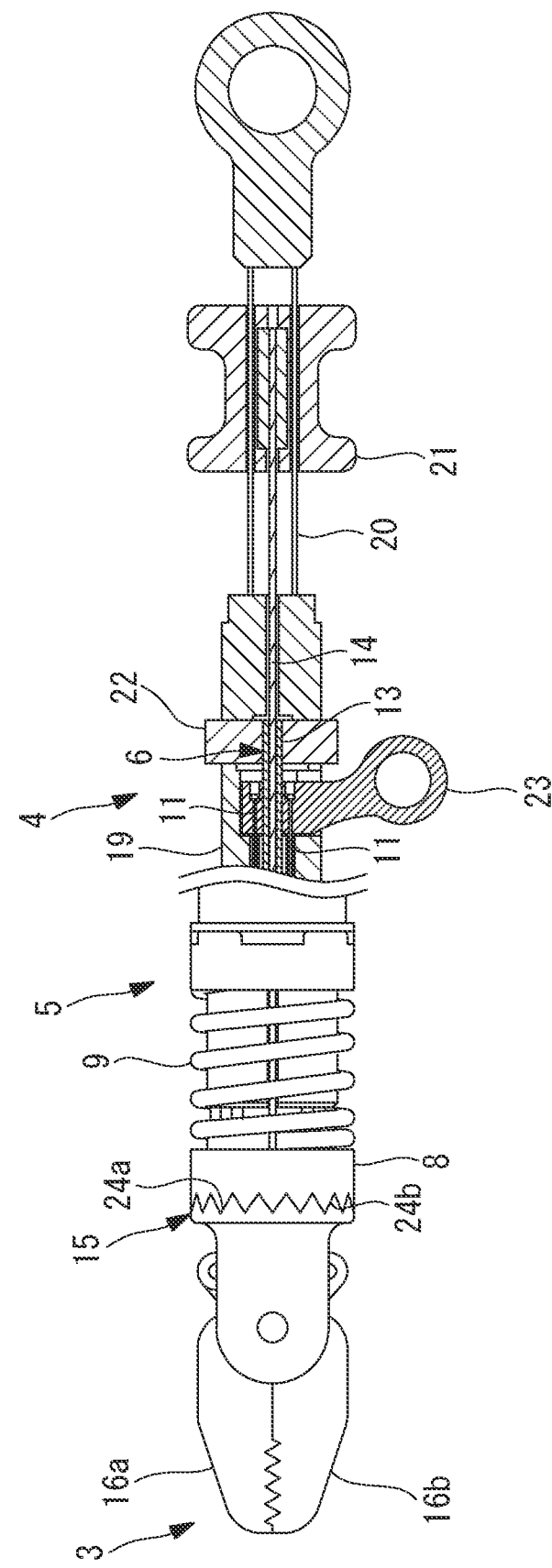
FIG. 11 is a diagram illustrating the state in which the moving unit and the base are joined in a third modification of the endoscope treatment tool illustrated in FIG. 1.
Figure 12:
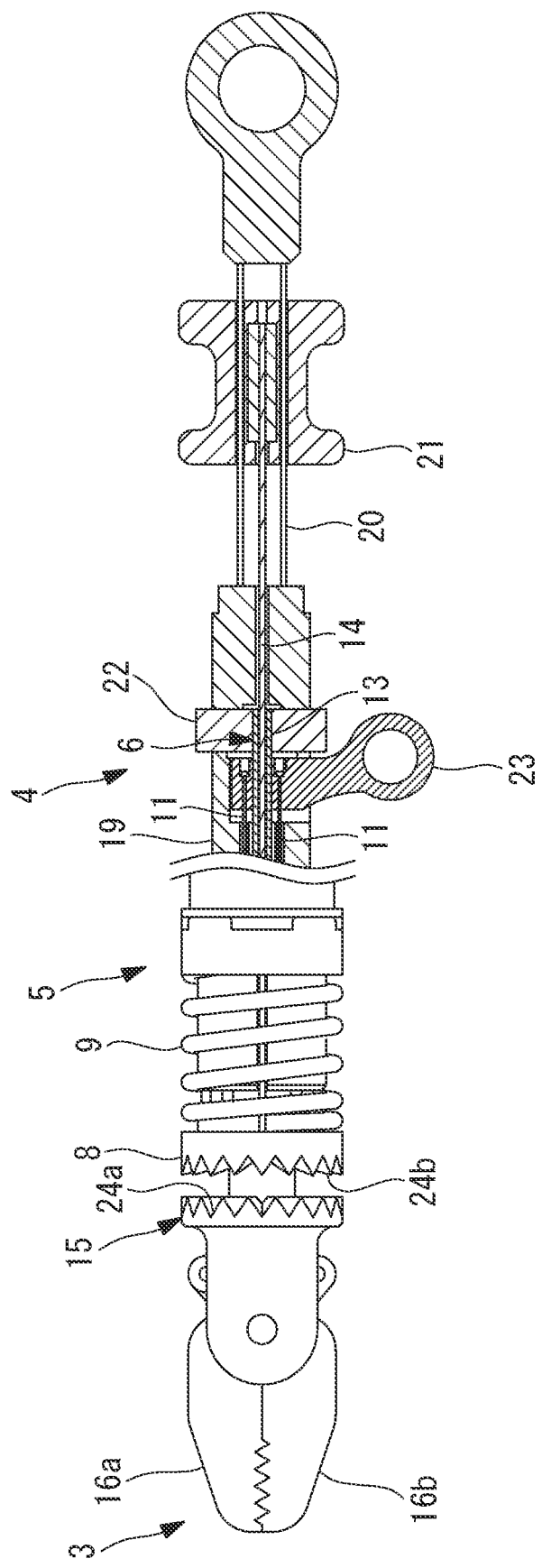
FIG. 12 is a diagram illustrating the state in which the moving unit and the base are separated from each other in the third modification of the endoscope treatment tool illustrated in FIG. 1.

In addition, although an example of restricting the rotation of the treatment unit 3 by bringing the flat distal end surface 5a of the moving unit 8 into close contact with the flat contact surface 3a is described, as illustrated in FIGS. 11 and 12, the moving unit 8 and the base 15 of the treatment unit 3 may mesh with each other through recesses and protrusions 24a and 24b formed thereon.

In this case, the base 15 has a portion that is in a more distal end side of the tubular part 18, that extends in the radially outward direction, and that has triangular wave-shaped recesses and protrusions 24a. The moving unit 8 also has triangular wave-shaped recesses and protrusions 24b complementary to the recesses and protrusions 24a of the base 15.

Then, as illustrated in FIG. 12, in the operation unit 4, the recesses and protrusions 24b of the moving unit 8 can be moved away from the recesses and protrusions 24a of the base 15 by applying a tension to the first wires 11 by moving the trigger 23 toward the proximal end side with respect to the operation unit body 19.

Meanwhile, as illustrated in FIG. 11, releasing the tension acting on the first wires 11 by freeing the trigger 23 brings the recesses and protrusions 24b of the moving unit 8 and the recesses and protrusions 24a of the base 15, which are triangular wave-shaped complementary recesses and protrusions, close to each other due to the elastic restoring force of the coil spring 9. As a result, at least the distal end portions of the recesses and protrusions 24a and 24b mesh with each other. Thus, a frictional force is generated at the position where the recesses and protrusions 24a and 24b mesh with each other, and thus the rotation of the treatment unit 3 can be restricted. Meshing preferably involves bringing the recesses and protrusions 24a and 24b into close contact with each other.

Figure 13:
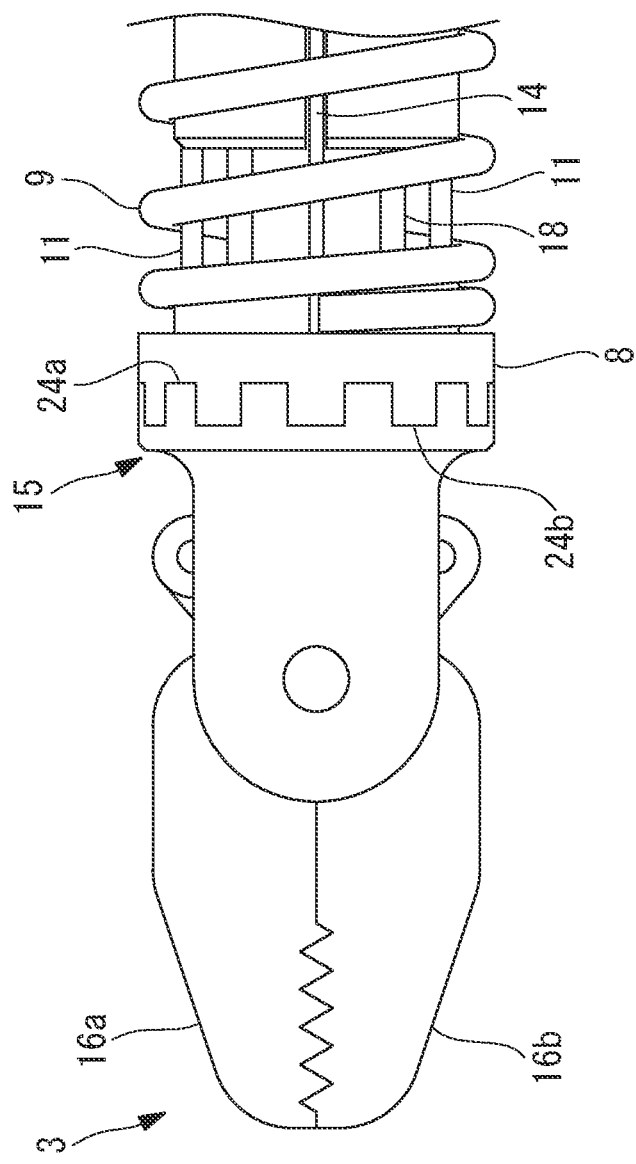
FIG. 13 is an enlarged view illustrating the state in which the moving unit and the base are joined in a fourth modification of the endoscope treatment tool illustrated in FIG. 1.

Alternatively, rectangular wave-shaped recesses and protrusions illustrated in FIG. 13 may be employed as the recesses and protrusions 24a and 24b instead of the complementary triangular wave-shaped recesses and protrusions.

In this manner, when the recesses and protrusions 24a and 24b of the moving unit 8 and the base 15 are meshed with each other, the rotational force about the longitudinal axis can be more smoothly transmitted than when the recesses and protrusions 24a and 24b are triangular wave-shaped.

Figure 14:
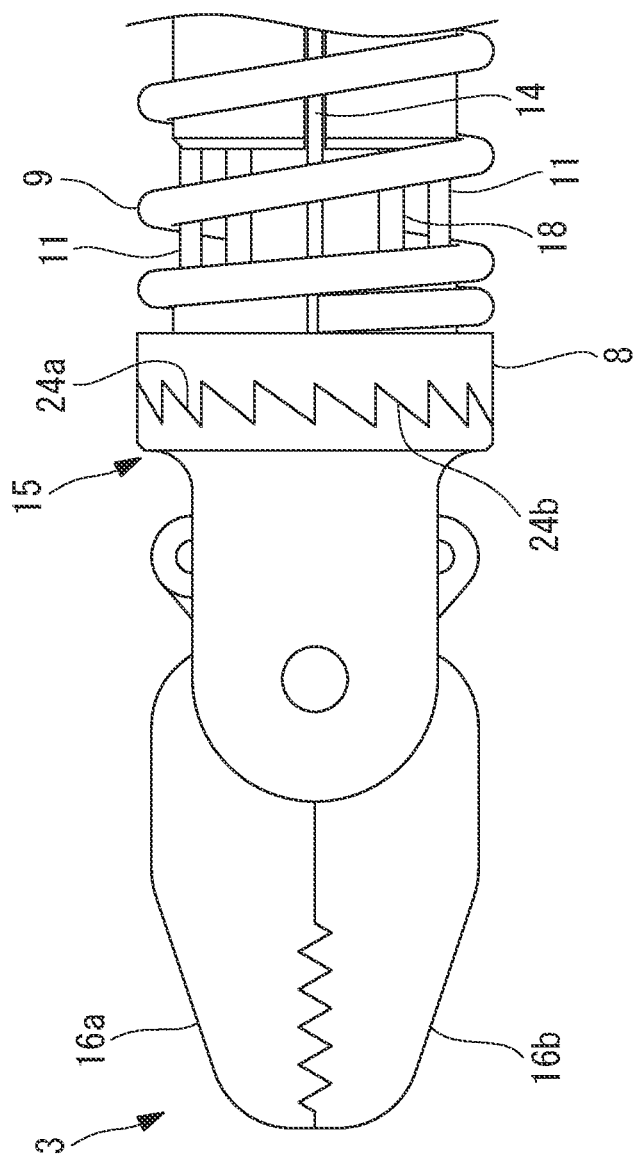
FIG. 14 is an enlarged view illustrating the state in which the moving unit and the base are joined in a fifth modification of the endoscope treatment tool illustrated in FIG. 1.

Alternatively, as illustrated in FIG. 14, recesses and protrusions having a sawtooth shape that allows unidirectional rotation may be employed as the recesses and protrusions 24a and 24b.

With the sawtooth shape, rotation in another direction about the longitudinal axis is restricted, and, when an excessively large torque acts on the treatment unit 3, the torque can be released by allowing rotation in one direction, and thus the insertion unit 2 can be prevented from becoming excessively twisted.

Alternatively, the flat distal end surface 5a of the moving unit 8 and the flat contact surface 3a may be subjected to a frictional coefficient-increasing treatment such as increasing the surface roughness.

Furthermore, although the coil spring 9 is described as an example of the urging member, a different elastic member or a magnet, for example, may be employed. Any material may be used for the coil spring 9.

Although forceps that include a pair of grasping pieces 16a and 16b that are pivotable are described as an example of the treatment unit 3, forceps that include one fixed grasping piece 16a and one pivotable grasping piece 16b may be employed instead. Furthermore, any treatment tool (for example, a hook, scissors, or a knife) can be used for the treatment as long as the treatment tool can receive the torque from the external force about the longitudinal axis.

The treatment unit 3 may include a joint. This is because the torque about the longitudinal axis caused by an external force can be smoothly received by bending the joint. The joint may be of any form, such as a link joint, a barrel joint, or a multilumen tube.

Figure 15:
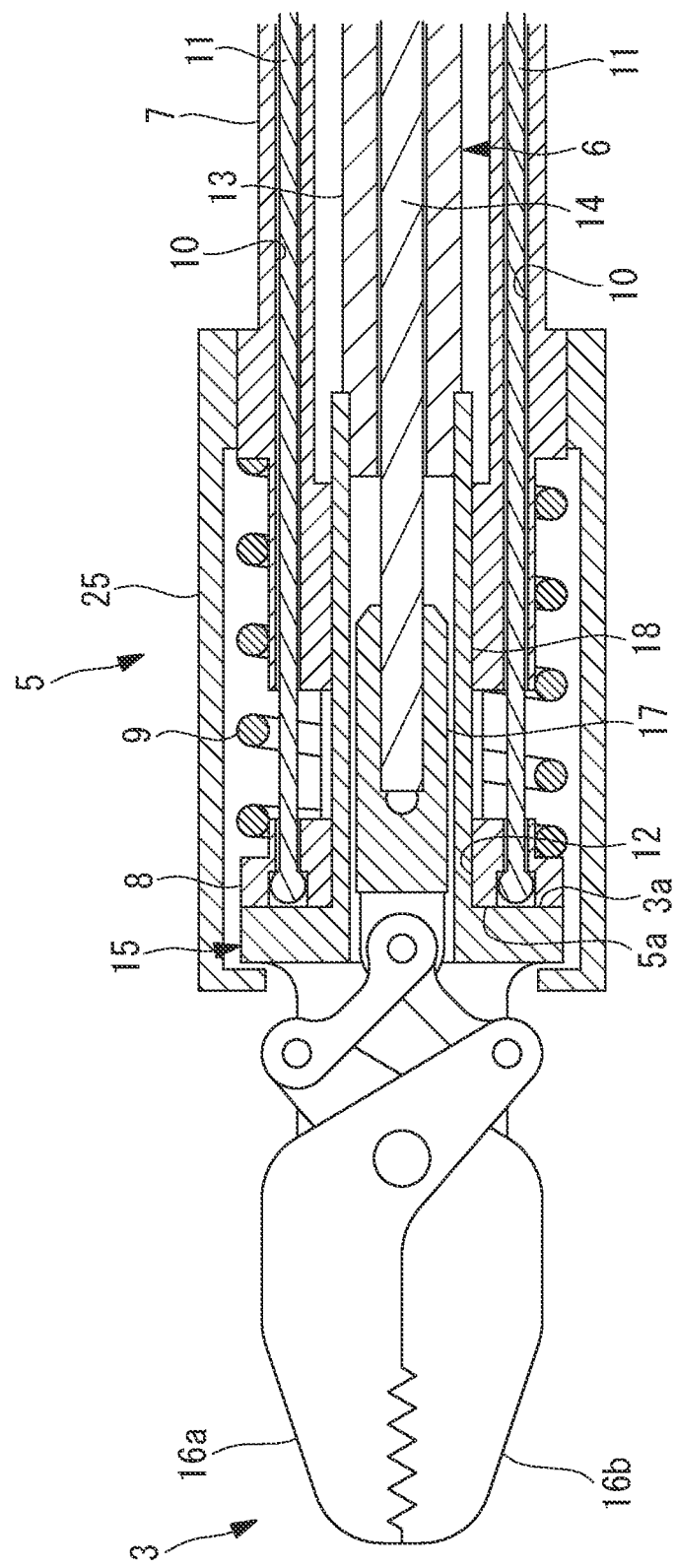
FIG. 15 is a side view illustrating a sixth modification of the endoscope treatment tool illustrated in FIG. 1.

As illustrated in FIG. 15, a cover 25 that covers the moving unit 8, the contact surface 3a, and the coil spring 9 in the outer radial direction may be provided. In this manner, entrapment of the peripheral tissue between the moving unit 8 and the contact surface 3a or between turns of the coil spring 9 can be prevented. The cover 25 may be fixed to the exterior member 5 or to the base 15.

Figure 16:
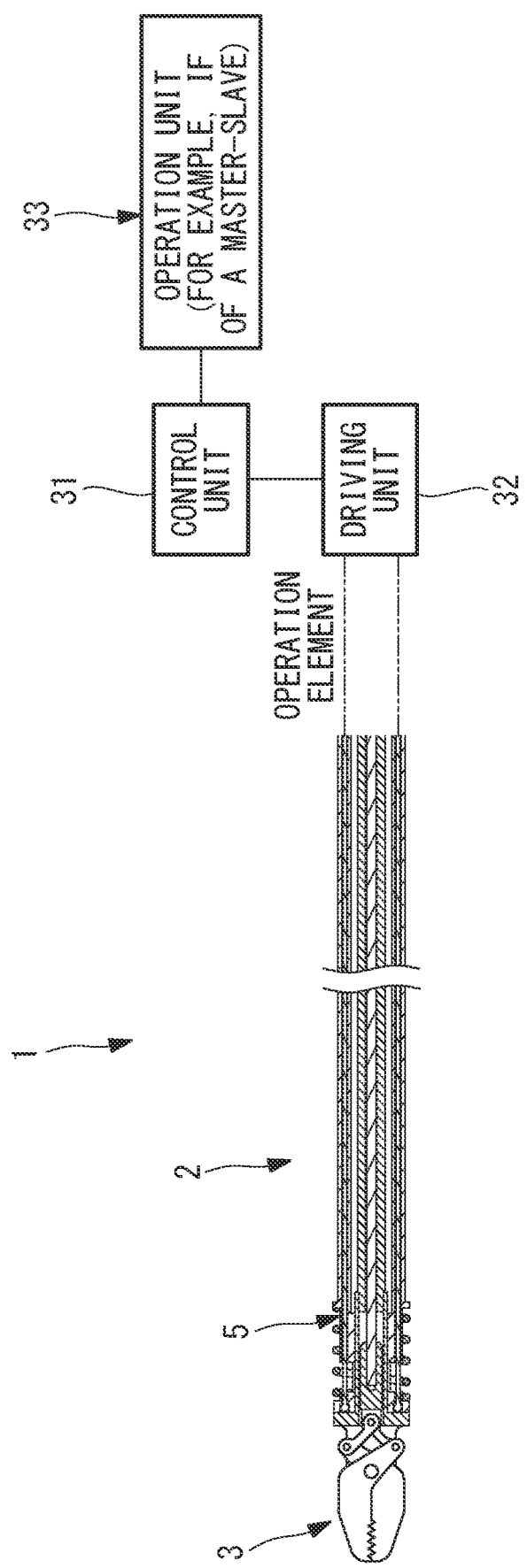
FIG. 16 is a side view illustrating a seventh modification of the endoscope treatment tool illustrated in FIG. 1.

Although an endoscope treatment tool 1 operated manually by maneuvering the operation unit 4 is described as an example of the present embodiment, as illustrated in FIG. 16, a master-slave-type endoscope treatment tool 1 operated by powered driving unit 32 may be employed instead. Movement of the moving unit 8, rotation of the treatment unit 3, and operation of the treatment unit 3 can be performed by a control unit 31 that controls the driving unit 32 on the basis of the operation amount of an operation unit 33 maneuvered by the operator.

Furthermore, although the body 7 described as an example of this embodiment includes four lumens 10 that are at four positions equally spaced from each other in the circumferential direction and penetrate the body 7 in the longitudinal axis direction, the structure is not limited to this as long as one lumen 10 that penetrates the body 7 in the longitudinal axis direction is provided in at least one place.

REFERENCE SIGNS LIST 1 endoscope treatment tool
2 insertion unit
3 treatment unit
3a contact surface (proximal end surface)
5 exterior member
5a distal end surface
6 operation member
7 body
8 moving unit
9 coil spring (urging member)
11 first wire (wire)
13 torque tube (rotation transmitting member)
14 second wire (another wire)
24a, 24b recesses and protrusions

The invention claimed is:
1. An endoscope treatment tool that is insertable into a channel of an endoscope, the endoscope treatment tool comprising:
an insertion unit having flexibility; and
a treatment unit disposed on a distal end of the insertion unit and supported so as to be rotatable about a longitudinal axis of the insertion unit, the insertion unit comprising:
a tubular exterior member configured to come into contact with the treatment unit on a distal end side of the insertion unit, the tubular exterior member configured to be moved in a direction of the longitudinal axis of the insertion unit;
an operation member penetrating through an interior of the exterior member, the operation member being configured to transmit rotation about the longitudinal axis to the treatment unit; and a wire penetrating through an interior of the insertion unit, the wire having a distal end fixed to the exterior member.

2. The endoscope treatment tool according to claim 1, wherein a proximal end surface of the treatment unit and a distal end surface of the exterior member are provided movable relative to each other in the direction of the longitudinal axis by pulling the wire toward a proximal end side to apply a tension.

3. The endoscope treatment tool according to claim 2, wherein friction generated between the proximal end surface of the treatment unit and the distal end surface of the exterior member maintains an amount of rotation about the longitudinal axis of the treatment unit with respect to the distal end surface of the exterior member.

4. The endoscope treatment tool according to claim 3, wherein the exterior member comprises:

a body;

a moving unit disposed in front of the body, the moving unit being supported to be movable in the direction of the longitudinal axis, the moving unit having the wire fixed thereto; and an urging member urging the moving unit to thrust forward with respect to the body.

5. The endoscope treatment tool according to claim 4, wherein a recess and a protrusion configured to mesh with each other when brought into close contact are provided on the proximal end surface of the treatment unit and the distal end surface of the exterior member.

6. The endoscope treatment tool according to claim 5, wherein the operation member comprises:

a tubular rotation transmitting member having a distal end to which the treatment unit is fixed; and a further wire penetrating an interior of the rotation transmitting member to be movable in the direction of the longitudinal axis, the further wire driving the treatment unit.

7. The endoscope treatment tool according to claim 6, wherein the rotation transmitting member comprises a torque tube.

\* \* \* \* \*